United States Patent [19]

Ciaudelli

[11] Patent Number: 4,639,369
[45] Date of Patent: * Jan. 27, 1987

[54] HIGHER ACYL LOWER ALKYL HYDROXYSTEARATES USEFUL IN COSMETICS

[75] Inventor: Joseph P. Ciaudelli, Ramsey, N.J.

[73] Assignee: Revlon, Inc., New York, N.Y.

[ * ] Notice: The portion of the term of this patent subsequent to Jan. 28, 2003 has been disclaimed.

[21] Appl. No.: 835,687

[22] Filed: Mar. 3, 1986

[51] Int. Cl.$^4$ .................. C11C 3/00; A61K 7/027; A61K 7/42; A61K 7/15
[52] U.S. Cl. ...................... 424/59; 260/405; 424/64; 424/65; 424/73; 514/785
[58] Field of Search ............... 260/410.9 M, 410.9 Q, 260/405; 514/785; 424/59, 64, 65, 78

[56] References Cited

U.S. PATENT DOCUMENTS

| | | | |
|---|---|---|---|
| 2,163,300 | 6/1939 | Wasson et al. | 260/410.9 Q |
| 2,218,026 | 10/1940 | Hansley | 260/410.9 Q |
| 2,256,353 | 9/1941 | Rheineck et al. | 260/405 |
| 2,397,008 | 3/1946 | Hunter et al. | 260/410.9 Q |
| 2,452,029 | 10/1948 | Bruson et al. | 260/405 |
| 2,500,918 | 3/1950 | Reuter et al. | 260/405 |
| 2,652,411 | 9/1953 | Teeter et al. | 260/405 |
| 3,308,140 | 3/1967 | Roe et al. | 260/405 |
| 3,792,066 | 2/1974 | Rothman et al. | 260/405 |
| 4,567,037 | 1/1986 | Ciaudelli | 424/59 |

FOREIGN PATENT DOCUMENTS 1952057 10/1969 Fed. Rep. of Germany .
162553 9/1983 Japan ........................ 260/410.9 R Primary Examiner—J. E. Evans

[57] ABSTRACT

Disclosed are fatty acid esters of the formula $CH_3(CH_2)_5CH(OCOR_1)(CH_2)_{10}COOR_2$ wherein, $R_1$ is a hydrocarbon radical having 17 carbon atoms with 1–3 double bond therein; and $R_2$ is a hydrocarbon radical having 1–4 carbon atoms.

10 Claims, No Drawings

HIGHER ACYL LOWER ALKYL HYDROXYSTEARATES USEFUL IN COSMETICS

BACKGROUND OF THE INVENTION

1. Field of the invention

This invention relates to high molecular weight diesters containing unsaturated hydrocarbon chains.

2. Description of the Prior Art

Organic esters, having the structure $R_1COOR$ wherein $R_1$ and $R$ are identical or different hydrocarbon chains, are widely distributed in nature and may be obtained from animal, vegetable and mineral sources. Such organic esters are in the form of liquid and solid fats, waxes and oils.

All natural fats and oils are mixtures of esters and are distinguished by their melting point range; the oils are liquid at ambient temperature due to the high percentage of unsaturated hydrocarbons in their molecules; the fats are solid or semi-solid. The esters of fats and oils, called triglycerides, are built upon glycerol as the alcohol moiety of the molecule, having the three hydrogens of glycerol replaced with fatty acid radicals. The acids found in fats and oils are straight chain, saturated or unsaturated monocarboxylic acids with four to twenty-six carbon atoms.

Waxes are also mixtures of esters, but differ from fats and oils in that they are monoesters of various alcohols with fatty acids. Most waxes are solids, containing large proportions of saturated fatty acids.

The organic esters are extensively used in cosmetic, household, industrial and pharmaceutical preparations. For example, the lower molecular weight esters are used as solvents in lacquers and nail enamels, perfumery, medicines and artificial flavorings.

While most of the esters can be obtained from natural sources, many lower molecular weight esters and some waxes are also produced synthetically. The synthetically produced esters are utilized analogously to the esters obtained from natural sources and are of great commercial importance.

An object of the present invention is to provide fatty acid esters based on hydroxystearic acid.

Another object of the present invention is to provide fatty acid esters for use in cosmetic compositions.

SUMMARY OF THE INVENTION

These and other objects are achieved by a fatty acid diester obtained by: first esterifying a hydroxystearic acid with a long chain unsaturated fatty acid to form an unsaturated esterified fatty acid; then, reacting the unsaturated esterified fatty acid with an alcohol to produce a diester of the present invention.

The fatty acid diesters of the present invention have the general formula $$CH_3(CH_2)_5CH(OCOR_1)(CH_2)_{10}COOR_2$$

wherein $R_1$ is a hydrocarbon radical having 17 carbon atoms with 1 to 3 double bonds; and $R_2$ is a hydrocarbon radical having 1 to 4 carbon atoms with straight or branched chains.

Examples of fatty acid diesters of the present invention include:
Methyl Oleoyl Oxystearate
Methyl Linoleoyl Oxystearate
Ethyl Oleoyl Oxystearate
Ethyl Linoleoyl Oxystearate
Propyl Oleoyl Oxystearate
Propyl Linoleoyl Oxystearate
Butyl Linolenoyl Oxystearate
Isopropyl Linoleoyl Oxystearate
Isopropyl Oleoyl Oxystearate
Isopropyl Linolenoyl Oxystearate
Butyl Oleoyl Oxystearate
Butyl Linoleoyl Oxystearate
Isobutyl Oleoyl Oxystearate
Isobutyl Linoleoyl Oxystearate

DETAILED DESCRIPTION OF THE INVENTION

The fatty acid diesters of the present invention and synthesis thereof will be illustrated by the examples that follow:

EXAMPLE 1

Isopropyl-12-Oleoyl Oxystearate (A) 500 grams of 12-hydroxystearic acid (Union Camp-Cenwax A), 440 grams of oleic acid (Emery-Emersol 233LL) and 7 grams of dibutyl tin oxide (Aldrich Chem. Co.) was mixed and heated to 190° C. in a 2-liter, 3-neck flask until the esterification reaction was completed. Water, which is formed during this esterification reaction was collected in a Dean-Stark trap. Upon completing the reaction, the acid number was determined and was found to be between 99 and 106, and the molecular weight was 564 for the product, 12-oleoyl oxystearic acid.

(B) The 12-oleoyl oxystearic acid obtained in A above is mixed with isopropanol. The mixture is heated and the water formed by the reaction is collected by a Dean-Stark trap. The reaction product, isopropyl-12-oleoyl oxystearate is recovered and filtered through a Buchner funnel.

It is to be noted, that the temperature used during the reaction may be lowered, and the reaction time may be shortened, by using a nitrogen sparge to drive water over during the esterification reaction.

EXAMPLE 2

Ethyl-12-Linoleoyl Oxystearate

The preparation of the title compound is analogous to the preparation in Example 1, except that, instead of oleic acid, linoleic acid (Emery's Emersol 315) is used, and ethanol is used instead of isopropanol.

EXAMPLE 3

Butyl-12-Linoleoyl Oxystearate

The title compound is prepared using 12-linoleoyl oxystearic acid and butyl alcohol according to the procedure described in Example 1.

The compounds of the present invention may be easily formulated into cosmetic compositions, household and pharmaceutical products.

In general, a cosmetic formulation for skin care comprises the following ingredients by weight:

1-20% of a fatty acid diester of the present invention or mixtures thereof;

5-10% of a humectant, such as glycerin, propylene glycol, sorbitol and mineral oil;

0.2–1.0% of a thickener, such as carboxyvinyl polimers, methyl cellulose, hydroxymethyl cellulose and hydroxypropyl cellulose;

0.5–10% of an emulsifier, such as sorbitan stearate, sorbitan palmitate, glyceryl stearate and glycol stearate; and 50–80% water.

In addition other ingredients, conventionally used in cosmetic preparations, may be used, such as preservatives, coloring agents and perfumes.

Examples 4, 5, 6 and 7 illustrate cosmetic compositions which can be made embodying the present invention.

EXAMPLE 4

Cosmetic Cream

|  | % w/w |
|---|---|
| Methyl 12-oleoyl oxystearate | 8.00 |
| Mineral Oil | 10.00 |
| Glycerol Monostearate | 10.00 |
| Methyl Paraben | 0.10 |
| Propyl Paraben | 0.15 |
| Perfume | 0.25 |
| Water | 71.50 |

EXAMPLE 5

Cosmetic Cream

|  | % w/w |
|---|---|
| Water | 61.25 |
| Carbopol 934 Solution | 5.00 |
| Ethyl Oleoyl Oxystearate | 8.00 |
| Propylene Glycol | 7.00 |
| Methyl Paraben | 0.30 |
| Propyl Paraben | 0.10 |
| Glyceryl Stearate | 4.00 |
| Cetyl Alcohol | 1.20 |
| Stearic Acid | 2.40 |
| Mineral Oil | 8.00 |
| Steareth 20 | 1.00 |
| Triethanolamine | 1.40 |
| Trisodium EDTA | 0.05 |
| Quaternium 15 | 0.10 |
| Dimethicone | 0.20 |

EXAMPLE 6

|  | % w/w |
|---|---|
| Isopropyl Linoleoyl Oxystearate | 8.00 |
| Cetyl Alcohol | 1.00 |
| Mineral Oil | 10.00 |
| Glyceryl Monostearate | 10.00 |
| Methyl Paraben | 0.10 |
| Propyl Paraben | 0.15 |
| Perfume | 0.25 |
| Water | 70.50 |

EXAMPLE 7

This example illustrates the compatibility of the diesters with other cosmetic ingredients: the formula contains both a suntanning agent and a sunscreening agent.

|  | % w/w |
|---|---|
| Isopropyl Linoleoyl Oxystearate | 4.00 |
| Mineral Oil | 8.00 |
| Glyceryl Monostearate SE | 8.00 |
| Cetyl Alcohol | 0.50 |
| Parsol MCX* | 5.00 |
| Propyl Paraben | 0.10 |
| Methyl Paraben | 0.15 |
| Unipertan P-24** | 5.00 |
| Perfume | 0.25 |
| Water | 69.00 |

*Tradename for Givaudan's 2-Ethylhexyl-p-methoxycinnamate
**Tradename for Induchem's Tyrosine complex.

Regarding cosmetic compositions, there may be mentioned in particular, those which are presented in the form of fluid emulsions, lotions, creams and lipstic bases. For example, the cosmetic compositions may be emollient milks or creams for face and hand care, make-up foundations, sunscreen milks or creams, antiperspirant milks or creams and shaving creams.

While various preferred embodiments of the present invention have been illustrated by means of specific examples, it is to be understood that the present invention is in no way to be deemed as limited thereto, but should be construed as broadly as defined by the appended claims.

What is claimed is:

1. A fatty acid ester of the formula $$CH_3(CH_2)_5CH(OCOR_1)(CH_2)_{10}COOR_2$$

wherein,
$R_1$ is a hydrocarbon radical having 17 carbon atoms with 1 to 3 double bonds therein; and
$R_2$ is a hydrocarbon radical having 1 to 4 carbon atoms.

2. The fatty acid ester of claim 1 wherein $R_1$ is oleyl.
3. The fatty acid ester of claim 1 wherein $R_1$ is linoleyl.
4. The fatty acid ester of claim 1 wherein $R_1$ is linolenyl.
5. The fatty acid ester of claim 1 wherein $R_1$ is oleyl and $R_2$ is isopropyl.
6. The fatty acid ester of claim 1 wherein $R_1$ is linoleyl and $R_2$ is isopropyl.
7. The fatty acid ester of claim 1 wherein $R_1$ is linoleyl and $R_2$ is ethyl.
8. The fatty acid ester of claim 1 wherein $R_1$ is oleyl and $R_2$ is n-butyl.
9. The fatty acid ester of claim 1 wherein $R_1$ is linoleyl and $R_2$ is isobutyl.
10. A cosmetic composition comprising by weight 1–20% of a fatty acid ester of the formula $$CH_3(CH_2)_5CH(OCOR_1)(CH_2)_{10}COOR_2$$

wherein,
$R_1$ is a hydrocarbon radical having 17 carbon atoms with 1 to 3 double bonds therein; and
$R_2$ is a hydrocarbon radical having 1 to 4 carbon atoms;
5–10% of an humectant;
0.2–1.0% of a thickener
0.5–10% of an emulsifier; and
50–80% water.

* * * * *